United States Patent [19]

Chou

[11] Patent Number: 5,401,861

[45] Date of Patent: Mar. 28, 1995

[54] LOW TEMPERATURE PROCESS FOR PREPARING ALPHA-ANOMER ENRICHED 2-DEOXY-2,2-DIFLUORO-D-RIBOFURANOSYL SULFONATES

[75] Inventor: Ta-Sen Chou, Indianapolis, Ind.

[73] Assignee: Eli Lilly and Company, Indianapolis, Ind.

[21] Appl. No.: 902,301

[22] Filed: Jun. 22, 1992

[51] Int. Cl.$^6$ ............................................ C07D 307/02
[52] U.S. Cl. ...................................... 549/476; 549/478
[58] Field of Search .......................... 549/475, 476, 478

[56] References Cited

U.S. PATENT DOCUMENTS 4,526,988  7/1985  Hertel .................................... 549/313
4,965,374  10/1990  Chou et al. ............................ 549/313

OTHER PUBLICATIONS

Brewster & McEwen *Organic Chemistry* pp. 528–529 (1961).
Hoffer, et al., *Chem. Ber.*, 93, 2777–2781 (1960).
Capon, B., *Chemical Reviews*, 69 (4), 440–41 (1969).
Hubbard, et al., *Nucleic Acids*, 12, 6827 (1984).

*Primary Examiner*—C. Warren Ivy
*Assistant Examiner*—A. A. Owens
*Attorney, Agent, or Firm*—Robert A. Conrad

[57] ABSTRACT

A stereoselective process for preparing alpha-anomer enriched 2-deoxy-2,2-difluoro-D-ribofuranosyl sulfonates by contacting a lactol with an amine base in an inert solvent, adjusting the temperature and adding a sulfonating reagent.

14 Claims, No Drawings

LOW TEMPERATURE PROCESS FOR PREPARING ALPHA-ANOMER ENRICHED 2-DEOXY-2,2-DIFLUORO-D-RIBOFURANOSYL SULFONATES

BACKGROUND OF THE INVENTION

1. Field of the Invention

This invention pertains to a low temperature process for making 2-deoxy-2,2-difluoro-D-ribofuranosyl-1-α-sulfonates for use as intermediates in the preparation of known anti-neoplastic and anti-viral agents.

2. State of the Art

Fluorine substitution has been investigated extensively in drug research and biochemistry as a means of enhancing the biological activity and increasing the chemical or metabolic stability of nucleosides. The replacement of a hydrogen by fluorine in a bioactive molecule is expected to cause minimal steric pertubations with respect to the molecule's mode of binding to receptors or enzymes and aid in overcoming the chemical and enzymatic instability problems of nucleosides. Difluorodeoxynucleosides are typically synthesized by coupling a 2-deoxy-2,2-difluoro-D-ribofuranosyl sulfonate with a purine or pyrimidine nucleobase.

U.S. Pat. No. 4,526,988 describes a process for making a hydroxy-protected 1-methanesulfonyl-2-deoxy-2,2-difluoro-D-ribofuranosyl derivative by reacting 3,5-bis(t-butyldimethyl silyoxy) hydroxy protected 2-deoxy-2,2-difluoro-D-ribofuranose dissolved in dichloromethane with methanesulfonyl chloride, in an equimolar amount of a suitable acid scavenger such as triethylamine for 3 hours at about 25° C. The resulting compound is coupled with a purine or pyrimidine base to form an anomeric mixture of nucleosides.

Pending U.S. patent application Ser. Nos. 07/902,302, Attorney Docket X-8406 and 07/902,312, Attorney Docket X-8236, both filed contemporaneously herewith, describe a stereoselective coupling process for preparing nucleosides which is believed to proceed via S$_N$2 displacement. In order to prepare beta-nucleosides via the S$_N$2 pathway, there is a need for a stereoselective process for preparing alpha-anomer enriched ribofuranosyl sulfonate intermediates for use in the synthesis of nucleosides.

Accordingly, one object of the present invention is to provide a stereoselective process for preparing alpha-anomer enriched ribofuranosyl sulfonates.

Another object of the present invention is to provide a stereoselective process for preparing alpha-anomer enriched ribofuranosyl sulfonates in yields higher than those previously achieved by conventional processes.

SUMMARY OF THE INVENTION

The present invention is a stereoselective process for preparing an alpha-anomer enriched ribofuranosyl derivative of the formula

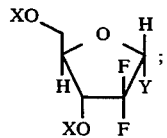

wherein each X is independently selected from hydroxy protecting groups and Y is selected from the group consisting of alkylsulfonyl and substituted alkylsulfonyl comprising contacting a lactol of the formula

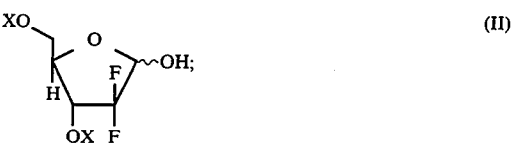

wherein X is as defined above; with an amine base in an inert solvent; adjusting the temperature; and adding a sulfonating reagent.

In another aspect, the invention is a stereoselective process for preparing an alpha-anomer enriched ribofuranosyl derivative of formula I by the above method with a sulfonating catalyst; wherein Y is selected from the group consisting of substituted arylsulfonyl.

DETAILED DESCRIPTION OF THE INVENTION

Throughout this document, all temperatures are in degrees Celsius, all proportions, percentages and the like, are in weight units and all mixtures are in volume units, except where otherwise indicated. Anomeric mixtures are expressed as a weight/weight ratio or as a percent. The term "xylenes" refers to all isomers of xylene and mixtures thereof. The term "lactol" alone or in combination refers to a 2-deoxy-2,2-difluoro-D-ribofuranose. The term "halo" alone or in combination refers to fluoro, chloro, bromo and iodo. The term "alkyl" alone or in combination refers to straight and branched chain aliphatic hydrocarbon groups which preferably contain up to 7 carbon atoms, such as, methyl, ethyl, n-propyl, isopropyl, n-butyl, t-butyl, n-pentyl, n-hexyl, 3-methylpentyl groups and the like or substituted straight and branched chain aliphatic hydrocarbons such as chloroethane, 1,2-dichloroethane, trifluoromethane and the like. The term "alkoxy" alone or in combination refers to compounds of the general formula AO; wherein A is an alkyl as defined above. The term "aryl" alone or in combination refers to phenyl and substituted derivatives thereof. The term "aromatic" alone or in combination refers to benzene-like structures containing (4n+2) delocalized π electrons. The term "sulfonate" or "sulfonyloxy" alone or in combination refers to compounds of the general formula BSO$_3$, wherein B is an alkyl or aryl group as defined above. The term "substituted" alone or in combination refers to the replacement of hydrogen or a common moiety by one or more of the groups selected from cyano, halo, carboalkoxy, toluoyl, nitro, alkoxy, alkyl, dialkylamino and electron-withdrawing groups such as a halo or nitro group. The phrase "anomer enriched" alone or in combination refers to an anomeric mixture wherein the ratio of a specified anomer is greater than 1:1 and includes substantially pure anomer.

The preparation of suitable lactol starting materials is described in U.S. Pat. No. 4,965,374 by Chou. In the present process the lactol is first treated with an amine base in an inert solvent at room temperature.

Suitable amine bases are selected from the group consisting of trimethylamine, triethylamine (Et$_3$N), tripropylamine, tributylamine, diisopropylethylamine, dimethylethylamine, diethylmethylamine, N-methylmorpholine, N,N-dimethylbenzylamine, 1,8-diazabicyclo[5.4.0]undec-7-ene, 1,5-diazabicyclo[4.3.0]non-5-ene, and mixtures thereof. The amine base preferably has a pKa from about 8 to about 20 and is employed in an equimolar amount relative to the amount of lactol used and more preferably from about 1.2 molar equivalents to about 2 molar equivalents.

The solvent employed in the present process preferably has a freezing point below about −78° C. and is selected from the group consisting of toluene, acetone, dichloromethane, glyme, tetrahydrofuran, 1-nitropropane, 2-nitropropane, dichlorofluoromethane, nitroethane, chloroform, freon, and mixtures thereof; more preferred is dichloromethane.

The temperature of the solvent mixture is then lowered to a temperature limited only by the freezing point of the solvent selected; more preferably the temperature is lowered to from about −40° C. to about −120° C. While not wishing to be bound by theory it is believed that the low temperature shifts the alpha to beta ratio of the lactol in base in favor of the alpha-anomer in a range of from about 2:1 to about 4:1 alpha to beta. In support of this theory, a compound of formula II, where X is benzoyl, was dissolved in dichloromethane. After adding triethylamine and stirring at room temperature for 30 minutes, the temperature of the reaction mixture was lowered. An $^{19}$F NMR analysis, taken at various temperatures, showed an increase in the alpha to beta ratio of the lactol as the temperature was lowered:

| Temperature | Alpha/Beta Ratio |
|---|---|
| 19° C. | 2.0:1 |
| −3° C. | 2.3:1 |
| −23° C. | 2.5:1 |
| −43° C. | 3.0:1 |
| −63° C. | 3.6:1 |
| −83° C. | 4.4:1 |

The ionized lactol is trapped in solution at the low temperature and higher alpha-anomer ratio by adding a sulfonating reagent to the solvent mixture forming the alpha-anomer enriched ribofuranosyl derivatives of formula I.

The sulfonating reagent is selected from the group consisting of alkylsulfonyl halide, substituted alkylsulfonyl halide, substituted arylsulfonyl halide, alkylsulfonyl anhydride, substituted alkylsulfonyl anhydride, and substituted arylsulfonyl anhydride. However, when a substituted arylsulfonyl halide or substituted arylsulfonyl anhydride is used, a catalyst such as 4-dimethylaminopyridine (DMAP), 4-pyrrolidinopyridine or a mixture thereof must be used in conjunction with the sulfonating reagent. Preferred alkylsulfonyl halides are selected from the group consisting of methanesulfonyl halide, ethanesulfonyl halide, 2-chloroethanesulfonyl halide. Preferred arylsulfonyl halides are selected from the group consisting of nitrobenzenesulfonyl halide, dinitrobenzenesulfonyl halide, bromobenzenesulfonyl halide and dibromobenzenesulfonyl halide.

Sulfonating catalysts are employed when bulky arylsulfonating reagents are used. The catalyst can be used alone as a catalyst and acid-scavenging agent, or used in combination with an amine base, such as triethylamine. Suitable sulfonating catalysts for example are 4-dimethylaminopyridine and 4-pyrrolidinopyridine.

The hydroxy protecting groups (X) are known in the art and are described in Chapter 3 of *Protective Groups in Organic Chemistry*, McOmie Ed., Plenum Press, New York (1973), and Chapter 2 of *Protective Groups in Organic Synthesis*, Green, John, J. Wiley and Sons, New York (1981); preferred are ester forming groups such as formyl, acetyl, substituted acetyl, propionyl, butynyl, pivaloyl, 2-chloroacetyl, benzoyl, substituted benzoyl, phenoxycarbonyl, methoxyacetyl; carbonate derivatives such as phenoxycarbonyl, t-butoxycarbonyl, ethoxycarbonyl, vinyloxycarbonyl, 2,2,2-trichloroethoxycarbonyl and benzyloxycarbonyl; alkyl ether forming groups such as benzyl, diphenylmethyl, triphenylmethyl, t-butyl, methoxymethyl, tetrahydropyranyl, allyl, tetrahydrothienyl, 2-methoxyethoxy methyl; and silyl ether forming groups such as trialkylsilyl, trimethylsilyl, isopropyldialkylsilyl, alkyldiisopropylsilyl, triisopropylsilyl, t-butyldialkylsilyl and 1,1,3,3-tetraisopropyldisloxanyl; carbamates such as N-phenylcarbamate and N-imidazoylcarbamate; however more preferred are benzoyl, mono-substituted benzoyl and disubstituted benzoyl, acetyl, pivaloyl, triphenylmethyl ethers, and silyl ether forming groups, especially t-butyldimethylsilyl; while most preferred is benzoyl.

The alpha-anomer enriched ribofuranose of formula I may be isolated in substantially pure form, i.e., greater than 95 percent purity, by the process described in Pending U.S. patent application Ser. No. 07/902,303, Attorney Docket X-7776, filed contemporaneously herewith. This process requires warming the alpha-anomer enriched ribofuranose in solvent at about 30° C. to about 70° C. to form a supersaturated solution. The solution temperature is then lowered to about 10° C. and a counter solvent is added to form pure alpha-anomer ribofuranose as solid crystals. The crystals are recovered from solution, for example, by filtration and dried.

The process is preferably carried out under an inert atmosphere at atomospheric conditions and is substantially complete in about 30 minute to about 24 hours.

The progress of the present process may be followed using high pressure liquid chromotography (HPLC) or NMR spectroscopy.

The following examples illustrate specific aspects of the present invention and are not intended to limit the scope thereof in any respect and should not be so construed.

EXAMPLE 1

Preparation of alpha-anomer enriched 2-deoxy-2,2-difluoro-D-ribofuranosyl-3,5-di-O-benzoyl-1-methanesulfonate To a solution of 2-deoxy-2,2-difluoro-D-ribofuranosyl-3,5-dibenzoate (40 mg) in CD$_2$Cl$_2$ (0.5 ml) was added triethylamine (0.025 ml). After stirring at room temperature for 30 minutes the entire mixture was cooled to −78° C. then methanesulfonyl chloride (0.01 ml) was added. The reaction temperature was maintained between −78° C. and −80° C. for 30 minutes then warmed to room temperature. HPLC analysis indicated that the reaction was complete. The anomeric ratio of the titled compound, as determined by $^{19}$F NMR analysis, was 4:1 alpha to beta.

EXAMPLE 2

Preparation of alpha-anomer 2-deoxy-2,2-difluoro-D-ribofuranosyl-3,5-di-O-benzoyl-1-methanesulfonate To a solution of 2-deoxy-2,2-difluoro-D-ribofuranosyl-3,5-dibenzoate (60 g, 95% pure) in dichloromethane (600 ml) was added triethylamine (31.5 ml, 1.5 eq.). After stirring at room temperature for 30 minutes the mixture was cooled to −78° C. After 5 minutes, methanesulfonyl chloride (14 ml, 1.2 eq.) in dichloromethane (140 ml) was added to the mixture. The reaction temperature was maintained between −78° C. and −80° C. under nitrogen for one hour. HPLC analysis indicated that the reaction was complete. The anomeric ratio of the titled compound, as determined by HPLC analysis, was 3.53:1 alpha to beta.

To isolate the titled compound the reaction mixture was washed with waters 1N HCl solution and 5% sodium bicarbonate solution (300 ml each). The organic layer was separated and dried over anhydrous magnesium sulfate. The titled compound (31.5 g) was obtained in a yield of 46 percent. mp 88°–89° C.; $[\alpha]_D$ (C 1.01, CHCl$_3$) +84.2°; $[\alpha]_{365nm}$ +302.0°; Elemental Analysis: C$_{20}$H$_{18}$O$_8$SF$_2$: (Calc.) C 52.63; H 3.98; F 8.33; S 7.02 (456.4) (Actual): C 52.92; H 3.82; F 8.33; S 7.30; $^1$H NMR (CDCl$_3$): δ=3.17 (CH$_3$), 4.66 and 4.76 (C-5H), 4.84 (C-4H), 5.57 (C-3H), 6.13 (C-1H); $^{13}$C NMR (CDCl$_3$): δ=40.22 (CH$_3$), 62.51 (C-5H), 71.03 (C-3H; $J_{c,F}$=18.3, 38.5 Hz), 82.75 (C-4H), 99.59 (C-1H; $J_{c,F}$=25.5, 48.3 Hz), 122.24 (C-2H; $J_{c,F}$=259, 286 Hz).

EXAMPLE 3

Preparation of alpha-anomer 2-deoxy-2,2-difluoro-D-ribofuranosyl-3,5-di-O-benzoyl-1-methanesulfonate To a solution of 2-deoxy-2,2-difluoro-D-ribofuranosyl-3,5-dibenzoate (172 g, 95% pure,) in dichloromethane (1315 ml) was added triethylamine (69.1 g, 1.5 eq.). After stirring at room temperature for 30 minutes the mixture was cooled to −78° C. A separate solution of methanesulfonyl chloride (63.0 g, 1.2 eq.) in dichloromethane (504 ml) was cooled to −20° C. and added under nitrogen over 3 to 5 minutes to maintain the temperature of the reaction mixture between −78° C. and −85° C. The reaction mixture was stirred for 50 minutes then slowly warmed to 0° C. HPLC analysis indicated that the reaction was complete. The anomeric ratio of the titled compound, as determined by HPLC analysis, was 3.76:1 alpha to beta.

To isolate the titled compound, the reaction mixture was washed with 1N aqueous HCl solution, 5 percent sodium bicarbonate solution and water (600 ml) then dried over magnesium sulfate. The organic layer was separated and dried under vacuum to give 152 g of the titled compound.

EXAMPLE 4

Preparation of alpha-anomer enriched 2-deoxy-2,2-difluoro-D-ribofuranosyl-3,5-di-O-benzoyl-1-(p-nitrobenzene) sulfonate To a solution of 2-deoxy-2,2-difluoro-D-ribofuranosyl-3,5-dibenzoate (100 mg), dichloromethane (1 ml) under nitrogen was added 4-dimethylaminopyridine (48 mg, 1.5 eq.). After stirring at room temperature for 30 minutes the mixture was cooled to −78° C. then stirred for 15 minutes and treated with a solution of p-nitrobenzenesulfonyl chloride (78 mg, 0.317 mM, 1.2 eq.) in dichloromethane (1 ml).

To isolate the titled compound the reaction mixture was added to 1N aqueous HCl. The organic layer was separated and washed with 5 percent sodium bicarbonate solution and water (1 ml) and dried over magnesium sulfate, filtered and concentrated to give a thick oil. An $^{19}$F NMR analysis of the oil indicated that the anomeric ratio of the titled compound was 1.57:1 alpha to beta.

EXAMPLE 5

Preparation of alpha-anomer enriched 2,deoxy-2,2-difluoro-D-ribofuranosyl-3,5-dibenzoyl-1-(2,4-dinitro benzene)sulfonate To a solution of 2-deoxy-2,2-difluoro-D-ribofuranosyl-3,5-dibenzoate (100 mg) in dichloromethane (1 ml) under nitrogen was added 4-dimethylaminopyridine (48 mg, 1.5 eq.). After stirring at room temperature for 30 minutes the mixture was cooled to −78° C. and stirred for 15 minutes then treated with a solution of 2,4-dinitrobenzenesulfonyl chloride (74.5 mg, 1.2 eq.) in dichloromethane (1 ml). Formation of the titled compound was verified by converting the 2,4-dinitrobenzenesulfonate to 2-deoxy-2,2-difluoro-D-ribofuranosyl-3,5-di-O-benzoyl bromide. This was carried out by adding tetrabutylammonium bromide to the reaction mixture at −78° C. immediately after adding the 2,4-dinitrobenzenesulfonyl chloride. An $^{19}$F NMR analysis revealed that the alpha to beta ratio of the bromo anomer was 1:2.2. Since the bromination was a $S_N2$ displacement, the anomeric ratio of the titled compound was calculated to be 2.2:1 alpha to beta.

The following Table shows the affects of the temperature and amine base on the anomeric ratio of the ribofuranosyl derivatives of formula I, prepared in accordance with the present process.

TABLE

| Sulfonating Reagent | Base | Temperature | α:β Ratio (I) |
|---|---|---|---|
| p-nitrobenzenesulfonyl chloride | Et$_3$N | 23° C. | 1:7 |
| p-nitrobenzenesulfonyl chloride | Et$_3$N | −78° C. | 1:7 |
| p-nitrobenzenesulfonyl chloride | DMAP | −78° C. | 2:1 |
| 2,4-dinitrobenzenesulfonyl chloride | Et$_3$N | −78° C. | 1:2 |
| 2,4-dinitrobenzenesulfonyl chloride | DMAP | −78° C. | 2:1 |
| Ethanesulfonyl chloride | Et$_3$N | 23° C. | 1:1.5 |
| Ethanesulfonyl chloride | Et$_3$N | −78° C. | 1.3:1 |
| 2-chloro-1-ethane sulfonyl chloride | Et$_3$N | 23° C. | 1:1 |
| 2-chloro-1-ethane sulfonyl chloride | Et$_3$N | −78° C. | 2.7:1 |

The ribofuranosyl derivative of Formula (I) in the above Table is the corresponding 2-deoxy-2,2-difluoro-D-ribofuranosyl-3,5-di-O-benzoyl-1-alkyl or -aryl sulfonate.

The present invention has been described in detail, including the preferred embodiments thereof. However, it will be appreciated that those skilled in the art, upon consideration of the present disclosure, may make modifications and/or improvements on this invention that fall within the scope and spirit of the invention as set forth in the following claims.

What is claimed is:

1. A stereoselective low temperature process for preparing an alpha-anomer enriched ribofuranosyl derivative of the formula

wherein each X is independently selected from hydroxy protecting groups and Y is selected from the group consisting of alkylsulfonate alkylsulfonate comprising contacting a lactol of the formula

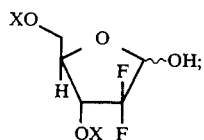

(II)

wherein X is as defined above; with an amine base in an inert solvent; lowering the temperature of the lactol solution in the range of about $-40°$ C. to about $-120°$ C. then adding a sulfonating reagent.

2. The process of claim 1 wherein the solvent is selected from the group consisting of toluene, acetone, dichloromethane, glyme, tetrahydrofuran, 1-nitropropane, 2-nitropropane, dichlorofluoromethane, nitroethane, chloroform, freon, and mixtures thereof.

3. The process of claim 2 wherein the solvent is selected from the group consisting of dichloromethane, chloroform, and mixtures thereof.

4. The process of claim 3 wherein the solvent is dichloromethane.

5. The process of claim 1 wherein the amine base is selected from the group consisting of trimethylamine, triethylamine, tripropylamine, tributylamine, diisopropylethylamine, dimethylethylamine, diethylmethylamine, N-methylmorpholine, N,N-dimethylbenzyl amine, 1,8-diazabicyclo[5.4.0]undec-7-ene, 1,5-diazabicyclo[4.3.0]non-5-ene, and mixtures thereof.

6. The process of claim 5 wherein the amine base is triethylamine.

7. The process of claim 5 wherein the amine base has a pKa of from about 8 to about 20.

8. The process of claim 1 wherein the amount of amine base is from about 1 equivalent to about 2 equivalents.

9. The process of claim 1 wherein the temperature is adjusted from about $-60°$ C. to about $-80°$ C.

10. The process of claim 1 wherein the sulfonating reagent is selected from the group consisting of alkylsulfonyl halide, substituted alkylsulfonyl halide, alkylsulfonyl anhydride, and substituted alkylsulfonyl anhydride.

11. The process of claim 10 wherein the alkylsulfonyl halide is selected from the group consisting of methanesulfonyl chloride, 2-chloroethanesulfonyl chloride and ethanesulfonyl chloride.

12. The process of claim 11 wherein the alkylsulfonyl halide is methanesulfonyl chloride.

13. The process of claim 1 further comprising preparing an alpha-anomer enriched ribofuranosyl derivative wherein Y is an arylsulfonate or substituted arylsulfonate group by adding a sulfonating reagent selected from the group consisting of substituted arylsulfonyl halides and substituted arylsulfonyl anhyrides and a sulfonating catalyst selected from 4-dimethylaminopyridine, 4-pyrrolidinopyridine, and mixtures thereof.

14. The process of claim 13 wherein the substituted arylsulfonyl halide is selected from nitrobenzenesulfonyl chloride, dinitrobenzenesulfonyl chloride, bromobenzenesulfonyl chloride and dibromobenzenesulfonyl chloride and the sulfonating catalyst is N,N-dimethylaminopyridine.

* * * * *

UNITED STATES PATENT AND TRADEMARK OFFICE
CERTIFICATE OF CORRECTION

PATENT NO. : 5,401,861
DATED : March 28, 1995
INVENTOR(S) : Ta-Sen Chou

It is certified that error appears in the above-indentified patent and that said Letters Patent is hereby corrected as shown below:

Column 6, line 67, "alkylsulfonate alkylsulfonate comprising" should read, -- alkylsulfonate and substituted alkylsulfonate comprising --.

Signed and Sealed this

Fifth Day of September, 1995

Attest:

BRUCE LEHMAN

Attesting Officer

Commissioner of Patents and Trademarks